United States Patent
Rezach

(10) Patent No.: US 10,441,324 B2
(45) Date of Patent: Oct. 15, 2019

(54) SPINAL CONSTRUCT AND METHOD

(71) Applicant: Warsaw Orthopedic, Inc, Warsaw, IN (US)

(72) Inventor: William Alan Rezach, Covington, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 44 days.

(21) Appl. No.: 15/239,472

(22) Filed: Aug. 17, 2016

(65) Prior Publication Data

US 2018/0049777 A1 Feb. 22, 2018

(51) Int. Cl.
*A61B 17/70* (2006.01)
*A61B 90/00* (2016.01)

(52) U.S. Cl.
CPC ...... *A61B 17/7082* (2013.01); *A61B 17/7034* (2013.01); *A61B 17/7035* (2013.01); *A61B 2090/037* (2016.02)

(58) Field of Classification Search
None
See application file for complete search history.

(56) References Cited

U.S. PATENT DOCUMENTS

| | | | |
|---|---|---|---|
| 5,207,678 A | 5/1993 | Harms et al. | |
| 5,575,792 A | 5/1996 | Errico et al. | |
| 5,609,593 A | 3/1997 | Errico et al. | |
| 5,609,654 A | 3/1997 | Le et al. | |
| 5,630,817 A | 5/1997 | Rokegem et al. | |
| 5,643,263 A | 7/1997 | Simonson | |
| 5,797,911 A | 8/1998 | Sherman et al. | |
| 5,885,285 A | 3/1999 | Simonson | |
| 5,947,967 A | 9/1999 | Barker | |
| 6,074,391 A | 6/2000 | Metz-Stavenhagen et al. | |
| 6,280,442 B1 | 8/2001 | Barker et al. | |
| 6,520,962 B1 | 2/2003 | Taylor et al. | |
| 6,562,038 B1 | 5/2003 | Morrision | |
| 6,572,613 B1 | 6/2003 | Morrison | |
| 6,579,292 B2 | 6/2003 | Taylor | |
| 6,648,887 B2 | 11/2003 | Ashman | |
| 6,685,705 B1 | 2/2004 | Taylor | |
| 6,755,830 B2 | 6/2004 | Minfelde et al. | |
| 6,872,209 B2 | 3/2005 | Morrison | |
| 7,066,939 B2 | 6/2006 | Taylor | |
| 8,585,741 B2 | 5/2013 | Gabelberger et al. | |
| 8,992,575 B1 | 3/2015 | Di Lauro et al. | |
| 9,314,274 B2 | 4/2016 | Amstutz | |
| 9,402,663 B2 | 8/2016 | Peterson et al. | |
| 2005/0159750 A1 | 7/2005 | Doherty | |

(Continued)

FOREIGN PATENT DOCUMENTS

FR 2827757 A1 1/2003
JP 2001252283 A 9/2001

*Primary Examiner* — Nicholas J Plionis

(57) ABSTRACT

A spinal construct comprises a fastener having a head. A member includes an inner surface defining a cavity configured for disposal of the head and a groove configured for disposal of a band. The band is engageable with the head to connect the fastener and the member. A longitudinal element is connectable to the member. A body is disposable with the longitudinal element and defines an implant cavity. A coupling member is engageable with the body. Implants, systems, instruments and methods are disclosed.

20 Claims, 15 Drawing Sheets

(56) References Cited

U.S. PATENT DOCUMENTS

| | | | |
|---|---|---|---|
| 2006/0084989 A1* | 4/2006 | Dickinson | A61B 17/7007 606/278 |
| 2008/0097447 A1* | 4/2008 | Biscup | A61B 17/7007 606/71 |
| 2008/0161854 A1* | 7/2008 | Bae | A61B 17/7007 606/246 |
| 2010/0168796 A1* | 7/2010 | Eliasen | A61B 17/7035 606/264 |
| 2011/0245877 A1* | 10/2011 | Pisharodi | A61B 17/7001 606/268 |
| 2012/0029568 A1* | 2/2012 | Jackson | A61B 17/702 606/264 |
| 2013/0012954 A1* | 1/2013 | Paroth | A61B 17/7037 606/104 |
| 2013/0268005 A1* | 10/2013 | Rezach | A61B 17/7053 606/263 |

* cited by examiner

SPINAL CONSTRUCT AND METHOD

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct comprises a fastener having a head. A member includes an inner surface defining a cavity configured for disposal of the head and a groove configured for disposal of a band. The band is engageable with the head to connect the fastener and the member. A longitudinal element is connectable to the member. A body is disposable with the longitudinal element and defines an implant cavity. A coupling member is engageable with the body. In some embodiments, implants, systems, instruments and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
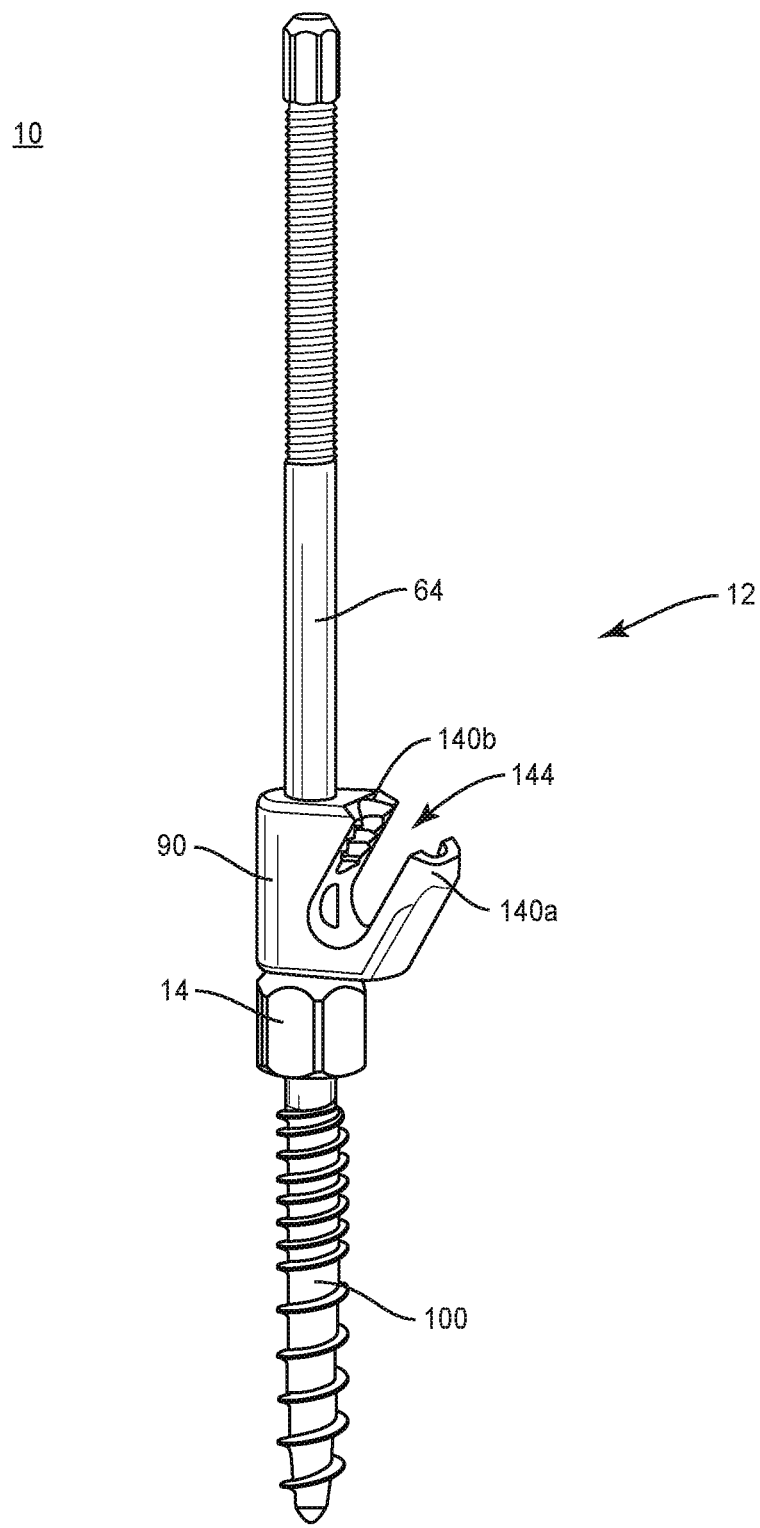
FIG. 1 is a perspective view of components of one embodiment of a surgical system in accordance with the principles of the present disclosure.

The exemplary embodiments of a surgical system and related methods of use disclosed are discussed in terms of medical devices for the treatment of musculoskeletal disorders and more particularly, in terms of a surgical system including a spinal construct. In some embodiments, the present system includes a spinal construct that facilitates dorsal reduction with vertebrae. In some embodiments, the present system is employed in applications for correction of deformities, such as, for example, kyphosis and scoliosis. In some embodiments, the present system provides adjustment and/or alignment of its component parts through multiple degrees of freedom and has locking capability to lock one or all of the components of the system in a selected position.

In some embodiments, the present system includes a spinal implant system having a spinal construct that selectively couples an implant to facilitate large dorsal reduction. In some embodiments, the spinal construct provides a posted connection to a screw within a modular system to allow functionality of a posted screw. In some embodiments, the spinal construct can be employed with a method to suspend or stop a reduction procedure at any point during the procedure such that there is no need to fully reduce a spinal rod. In some embodiments, the spinal implant system includes alternate adaptors such that a portion of a spinal construct can have a multi-axial or a uni-axial joint.

In some embodiments, the spinal construct comprises a posted system that allows a connector to be selectively disposed in a dorsal orientation such that the connector can be selectively adjusted and locked along a post. In some embodiments, the spinal construct allows medial/lateral adjustment for locking of its components.

In some embodiments, the spinal construct comprises a connector, a reduction post, an adaptor and a universal screw. In some embodiments, the adaptor can include multi-axial movement. In some embodiments, the adaptor can include uni-axial movement. In some embodiments, the adaptor is connected to the screw in a push-on configuration. In some embodiments, the adaptor includes a body, a crown and a ring.

In some embodiments, the spinal implant system is employed with a method for attaching a reduction post with the adaptor and the screw. In some embodiments, the method includes the step of threading the post with the adaptor. In some embodiments, the body of the adaptor includes keyed features on an external surface configured as a counter-torque when threading the post into a body. In some embodiments, the post is threaded and has an upper break-off torque feature to tighten a multi-axial joint of the adaptor and screw. In some embodiments, the post has a lower/base torque feature, for example, a hex surface, to allow for a revision procedure, for example, after a breakoff feature has been removed.

In some embodiments, the method includes the step of sliding the connector onto the post. In some embodiments, the method includes the step of adjusting the connector to a position where a spinal rod is loaded with the spinal construct and reduction instruments are employed to pull vertebrae to the spinal rod. In some embodiments, the connector has a counter-bore to allow it to seat down around a lower reduction post torque feature to reduce overall profile of the spinal construct. In some embodiments, the spinal rod presses against the reduction post when a setscrew is torqued with the connector to lock the connector and the post.

In some embodiments, the spinal implant system is employed with a method for treating a spine including the step of assembling a multi-axial adaptor onto a bone screw, for example, on a surgical table. In some embodiments, the method includes the step of placing the bone screw and multi-axial adaptor with vertebrae. In some embodiments, the method includes the step of threading the post into the multi-axial adaptor, for example, with a counter torque instrument. In some embodiments, the method includes the step of loading the connector onto the post. In some embodiments, the method includes the step of inserting the rod and the setscrew in a provisional attachment or fixation. In some embodiments, the method includes the step of reducing the connector and/or spinal rod using reduction instruments. In some embodiments, the method includes the step of tightening the multi-axial joint of the adaptor and the screw by twisting the reduction post and, in some cases, using the breakoff feature and/or a counter-torque instrument. In some embodiments, the method includes the step of tightening the setscrew to lock the connector on the reduction post. In some embodiments, the method includes the step of breaking off the reduction post breakoff feature.

In some embodiments, the spinal implant system is employed with a method for treating a spine including the step of placing the bone screw with vertebrae. In some embodiments, the method includes the step of assembling a multi-axial adaptor onto the bone screw. In some embodiments, the method includes the step of threading the post into the multi-axial adaptor, for example, with a counter torque instrument. In some embodiments, the method includes the step of loading the connector onto the post. In some embodiments, the method includes the step of inserting the rod and the setscrew in a provisional attachment or fixation. In some embodiments, the method includes the step of reducing the connector and/or spinal rod using reduction instruments. In some embodiments, the method includes the step of tightening the multi-axial joint of the adaptor and the screw by twisting the reduction post and, in some cases, using the breakoff feature and/or a counter-torque instrument. In some embodiments, the method includes the step of tightening the setscrew to lock the connector on the reduction post. In some embodiments, the method includes the step of breaking off the reduction post breakoff feature.

In some embodiments, the spinal implant system is employed with a method for treating a spine including the step of placing the bone screw with vertebrae. In some embodiments, the method includes the step of assembling a multi-axial adaptor with a threaded post and a connector on a surgical table. In some embodiments, the method includes the step of inserting the rod and the setscrew in a provisional attachment or fixation. In some embodiments, the method includes the step of reducing the connector and/or spinal rod using reduction instruments. In some embodiments, the method includes the step of tightening the multi-axial joint of the adaptor and the screw by twisting the reduction post and, in some cases, using the breakoff feature and/or a counter-torque instrument. In some embodiments, the method includes the step of tightening the setscrew to lock the connector on the reduction post. In some embodiments, the method includes the step of breaking off the reduction post breakoff feature.

In some embodiments, the spinal implant system comprises a modular system. In some embodiments, the spinal implant system comprises an adaptor component that is pre-assembled with a bone screw. In some embodiments, the spinal implant system comprises adaptor assemblies and screw assemblies that may be joined together during manufacturing or intra-operatively, such as, for example, during a surgical procedure in an operating room.

In some embodiments, a bone screw includes a head having a base and a screw shaft. In some embodiments, an adaptor includes a crown, a body and a snap ring. In some embodiments, a snap ring is engaged in a retaining groove in the body and provisionally engaged to the crown. In some embodiments, a snap ring is engaged to a part, such as, for example, a sleeve that maintains the snap ring centered. In some embodiments, the present system is employed with a method of assembly such that during assembly a head assembly drives and/or translates the crown or sleeve upwards to force the snap ring to expand and disengage the crown. In some embodiments, the method includes the step of engaging the head with the adaptor such that the snap ring engages a retaining groove in the adaptor and creates a permanent assembly of a bone fastener.

In some embodiments, the present system is employed with a method of assembly including the step of initially engaging the adaptor with a head of a bone screw. In some embodiments, the method includes the step of expanding a snap ring such that the snap ring is expanded by the head forcing a crown upwards in the adaptor. In some embodiments, this configuration allows the crown to disengage from the snap ring. In some embodiments, the method includes the step of collapsing the snap ring such that as the head travels into the adaptor, the snap ring collapses in a retaining groove and the bone fastener is permanently assembled.

In some embodiments, the spinal implant system comprises a spinal construct that can be assembled on a surgical table or in-situ. In some embodiments, the spinal construct is assembled with a force of less than 50 Newtons (N). In some embodiments, the spinal construct is selectively coupled with a non-instrumented assembly. In some embodiments, the non-instrumented assembly comprises manually engaging a head of a bone screw with the adaptor. In some embodiments, the non-instrumented assembly comprises manually engaging the head in a pop-on engagement with the adaptor. In some embodiments, a force required to manually engage the head with the adaptor in a non-instrumented assembly is in a range of 2 to 50 N. In some embodiments, a force required to manually engage the head with the adaptor in a non-instrumented assembly is in a range of 5 to 10 N. In some embodiments, a head of a bone screw is manually engaged with the adaptor in a non-instrumented assembly, as described herein, such that removal of the screw receiver from the head requires a force and/or a pull-out strength of at least 5000 N. In some embodiments, this configuration provides manually engageable components of a bone fastener that are assembled without instrumentation, and subsequent to assembly, the assembled components have a selected pull-out strength and/or can be pulled apart, removed and/or separated with a minimum required force.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal construct 12. Spinal implant system 10 is employed, for example, with an open or mini-open, minimal access and/or minimally invasive including percutaneous surgical technique and includes one or more spinal constructs 12 for treatment at a surgical site within a body of a patient, for example, a section of a spine to treat various spine pathologies, such as those described herein. In some embodiments, the components of spinal implant system 10 are configured to deliver and introduce components of one or more spinal constructs 12 that include implants, such as, for example, one or more adaptors, receivers, spinal rods, bodies, sleeves, posts, connectors, plates and/or fasteners. Spinal construct 12 forms one or more components of a surgical treatment implanted with tissue for positioning and alignment to stabilize a treated section of vertebrae. In some embodiments, spinal construct 12 provides one or more selectively coupled components and/or implants to facilitate large dorsal reduction, as described herein. In some embodiments, spinal construct 12 provides a posted screw connection with a fastener and a spinal rod, in a modular system to utilize the functionality of the posted screw, as described herein. In some embodiments, spinal construct 12 includes a post that allows a connector and/or a spinal rod connected therewith to be selectively reduced and/or disposed in a selected dorsal orientation relative to tissue. In some embodiments, spinal construct 12 includes a post that allows a connector and/or a spinal rod to be selectively reduced and/or adjusted and locked along the post. In some embodiments, spinal construct 12 allows medial/lateral adjustment for locking of its components.

Figure 4:
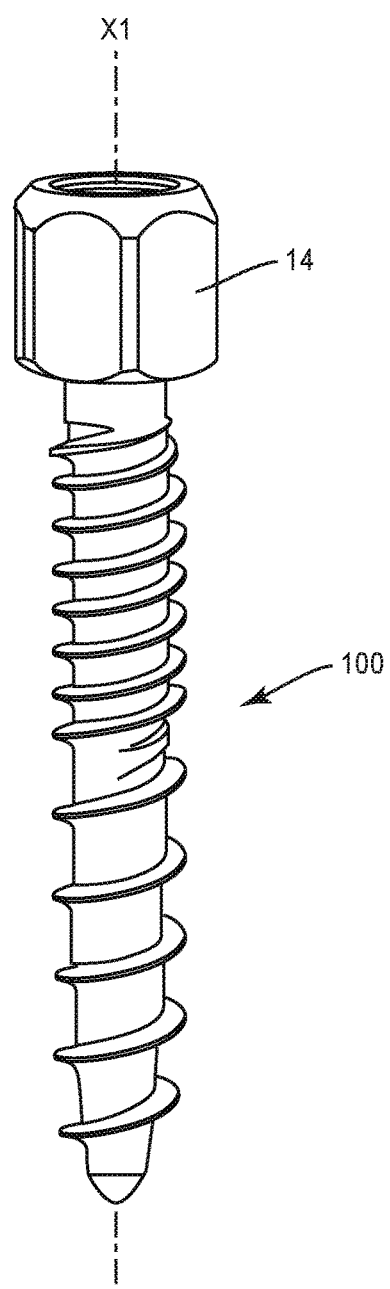
FIG. 4 is a perspective view of the components shown in FIG. 1.

Spinal construct 12 includes a fastener, such as, for example, a bone screw 100 connectable with a member, such as, for example, an adaptor 14. Adaptor 14 includes a wall 16. Wall 16 includes an inner surface 18 that defines a cavity 20. Cavity 20 is configured for disposal of a head 102 of bone screw 100, as described herein. Wall 16 extends along an axis X1, as shown in FIG. 4. In some embodiments, wall 16 may extend in alternate configurations relative to axis X1, such as, for example, arcuate, offset, staggered and/or angled portions. Cavity 20 is substantially circular. In some embodiments, all or only a portion of cavity 20 may have alternate cross section configurations, such as, for example, closed, V-shaped, W-shaped, oval, U-shaped, oblong, polygonal, irregular, uniform, non-uniform, offset, staggered, and/or tapered. In some embodiments, spinal construct 12 may include one or a plurality of adaptors 14.

Figure 5:
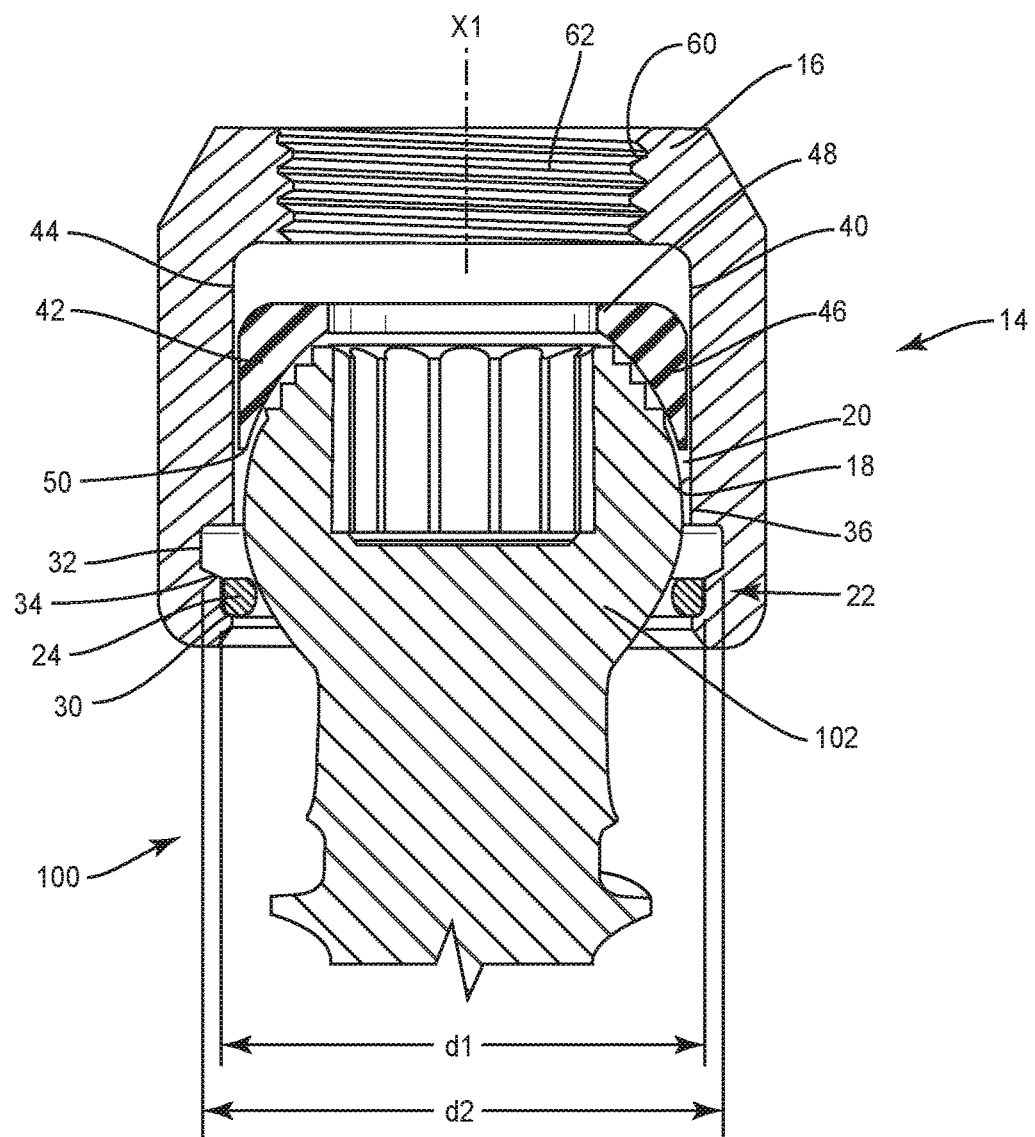
FIG. 5 is a cross section view of the components shown in FIG. 4.
Figure 6:
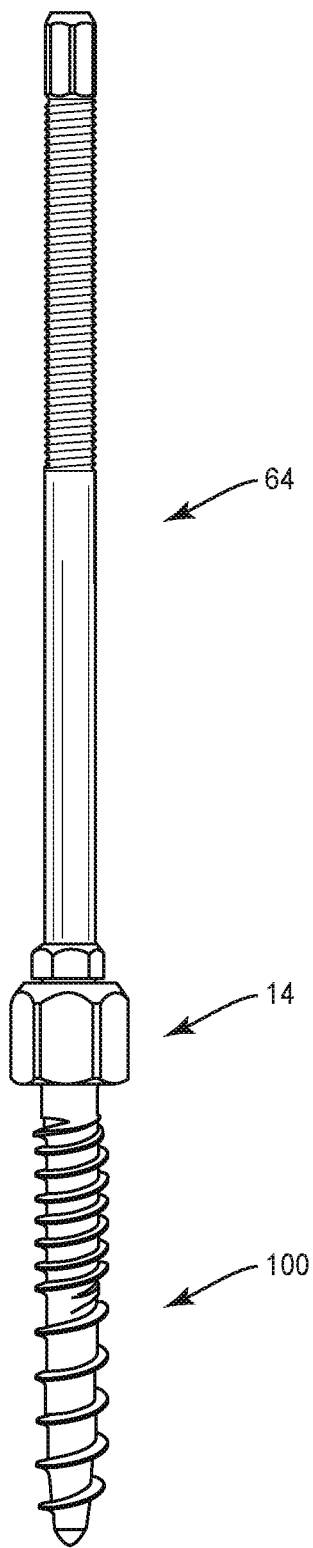
FIG. 6 is a side view of components of one embodiment of a surgical system in accordance with the principles of the present disclosure.
Figure 7:
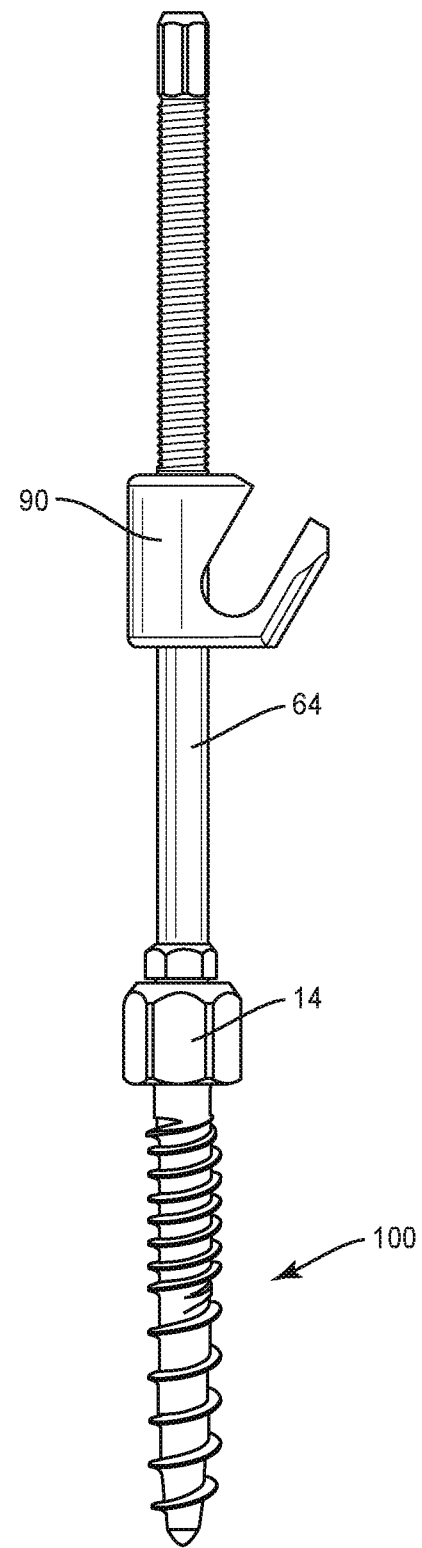
FIG. 7 is a side view of components of one embodiment of a surgical system in accordance with the principles of the present disclosure.
Figure 8:
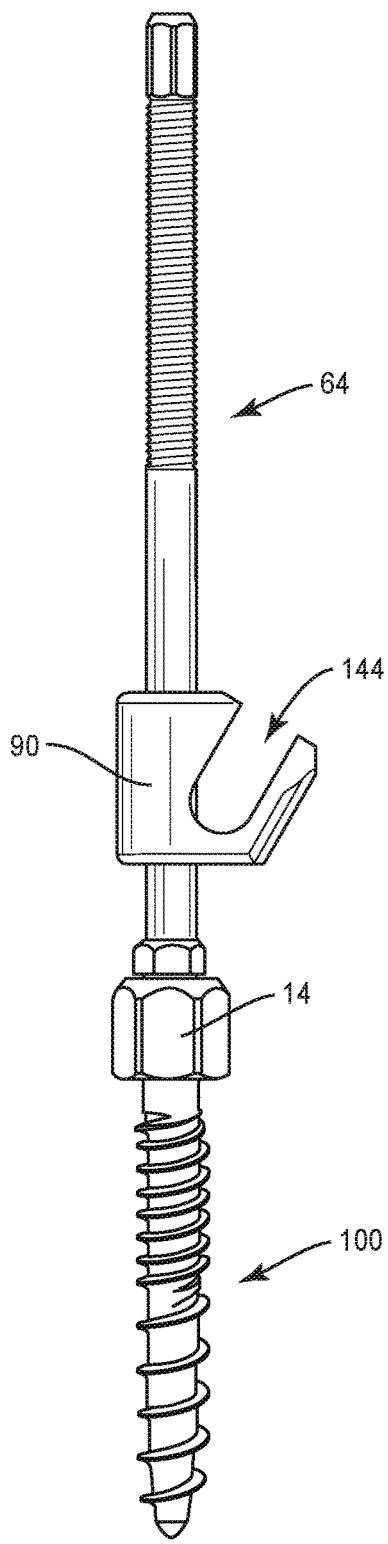
FIG. 8 is a side view of the components shown in FIG. 7.
Figure 9:
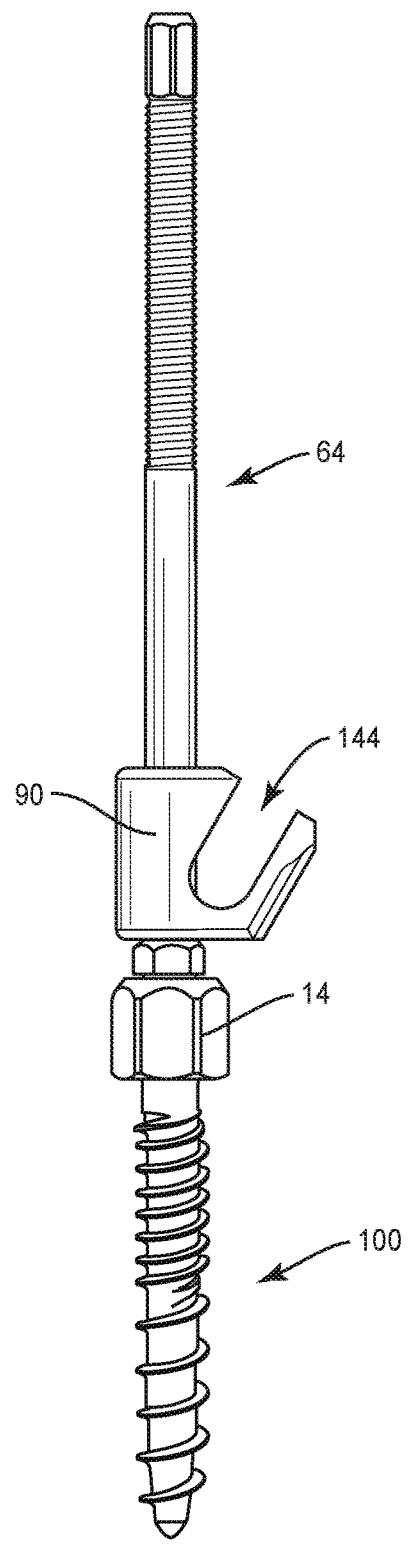
FIG. 9 is a side view of the components shown in FIG. 7.
Figure 10:
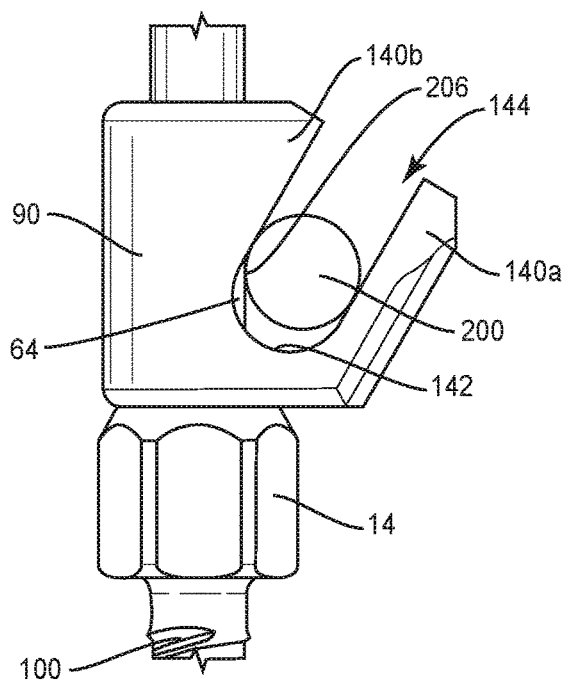
FIG. 10 is an enlarged break away view of the components shown in FIG. 9.

Surface 18 defines a groove 22 configured for disposal of a band, such as, for example, a circumferential ring 24. Ring 24 includes a circumference that extends between ends defining an opening, such as, for example, a gap (not shown), which facilitates expansion and contraction. Groove 22 includes a portion, such as, for example, a circumferential channel 30 having a diameter d1 and a portion, such as for, example, a circumferential channel 32 having a diameter d2, as shown in FIG. 5. In some embodiments, diameter d2 is greater than diameter d1.

Channel 32 is disposed adjacent and proximal to channel 30. Channel 32 is separate from channel 30 by a protrusion, such as, for example, a lip 34. In some embodiments, bone screw 100 is manually engageable with adaptor 14 and/or bone screw 100 is coupled with adaptor 14 in a non-instrumented assembly such that ring 24 translates from and into channels 30, 32, and over lip 34, as described herein. Ring 24 is expandable and resilient between a contracted and/or capture orientation and an expanded orientation, as described herein. In some embodiments, ring 24 facilitates manual engagement of adaptor 14 and bone screw 100 such that adaptor 14 is attached with bone screw 100 in a non-instrumented assembly, as described herein.

In some embodiments, surface 18 includes an engagement surface 36 that defines a mating element (not shown). In some embodiments, the mating element defines a particularly configured engagement surface configured to interface in a selective mating engagement with bone screw 100, as described herein. The mating element is configured to capture head 102 of bone screw 100. In some embodiments, the mating element can include arcuate surfaces and planar surfaces configured to interface with head 102 of bone screw 100 in a keyed connection. In some embodiments, the mating element is configured to resist and/or prevent rotation of bone screw 100 about a selected axis. In some embodiments, engagement surface 18 includes flats and/or arcuate surfaces to form various bone screw configurations, such as, for example, multi-axial screws, sagittal angulation screws, pedicle screws, mono-axial screws, uni-planar screws, fixed screws, anchors, tissue penetrating screws, conventional screws, expanding screws. In some embodiments, head 102 is slidably engageable with engagement surface 18 such that bone screw 100 is rotatable along a plurality of axes relative to adaptor 14 including rotation about axis X1.

In some embodiments, wall 16 defines a slot 40 configured for disposal of a part, such as, for example, a crown 42, as described herein. Slot 40 is defined by a surface 44 of wall 16. In some embodiments, all or only a portion of surface 44 may have alternate surface configurations to enhance engagement with crown 42, such as, for example, rough, arcuate, undulating, mesh, porous, semi-porous, dimpled and/or textured.

Crown 42 includes a wall 46 having an end surface 48 and an end surface 50, as shown in FIG. 5. Surface 48 is configured for engagement with a longitudinal element, such as, for example, a post 64, as described herein. Surface 50 defines a curved portion of crown 42 engageable with bone screw 100, as described herein. In some embodiments, all or only a portion of surface 50 may have alternate cross section configurations, such as, for example, oval, oblong, polygonal, irregular, uniform, non-uniform, offset, staggered, and/or tapered.

Adaptor 14 includes an inner surface 60. A portion of surface 60 includes a thread form 62. Thread form 62 is configured for engagement with post 64 to fix position and/or orientation of bone screw 100 relative to adaptor 14, as described herein. In some embodiments, surface 60 may be disposed with post 64 in alternate fixation configurations, such as, for example, friction fit, pressure fit, locking protrusion/recess, locking keyway and/or adhesive. In some embodiments, all or only a portion of surface 60 may have alternate surface configurations to enhance engagement with post 64, such as, for example, rough, arcuate, undulating, mesh, porous, semi-porous, dimpled and/or textured.

Figure 2:
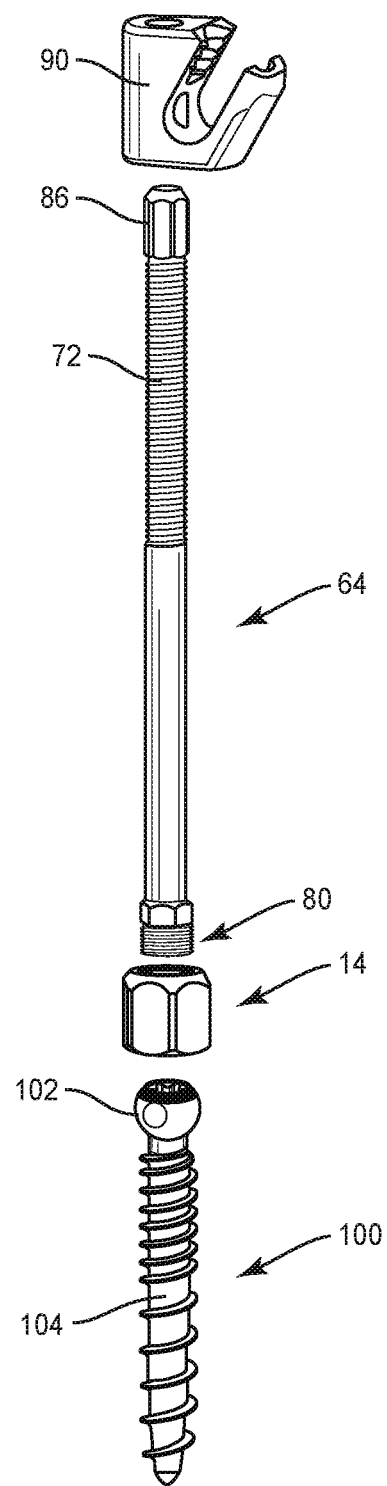
FIG. 2 is a perspective view of the components shown in FIG. 1 with parts separated.

Post 64 includes a portion 72, as shown in FIG. 2. In some embodiments, portion 72 is threaded for engagement with one or more components of spinal implant system 10, for example, a surgical reduction instrument, as described herein. In some embodiments, post 64 includes a break off or fracture surface, for example a selection location of portion 72, which is selectively disposed along the length of post 64 to selectively fix one or more components of spinal construct 12 relative to tissue, as described herein. In some embodiments, the break off or fracture surface can include a pre-determined fracture location, break off zone, frangible connection, reduced diameter portion and/or location along post 64 to be sheared with a surgical instrument. In some embodiments, post 64 is configured for threaded engagement with surface 60. In some embodiments, the break off or fracture surface is fabricated from a fracturing and/or frangible material such that manipulation of post 64 can fracture and separate the break off or fracture surface at a predetermined force and/or torque limit, as described herein. In some embodiments, as force and/or torque is applied to the break off or fracture surface and resistance increases, for example, due to fixation of post 64 with surface 60, as described herein, the predetermined torque and force limit is approached. In some embodiments, portion 72 is offset with post 64.

In some embodiments, portion 72 can fracture and separate at a predetermined force or torque limit, which may be in a range of approximately 6.7 Newton meter (Nm) to 13.5 Nm. In some embodiments, portion 72 may have the same or alternate cross section configuration as post 64, may be fabricated from a homogenous material or heterogeneously fabricated from different materials, and/or alternately formed of a material having a greater degree, characteristic or attribute of plastic deformability, frangible property and/or break away quality to facilitate fracture and separation of a selected location of post 64.

Figure 11:
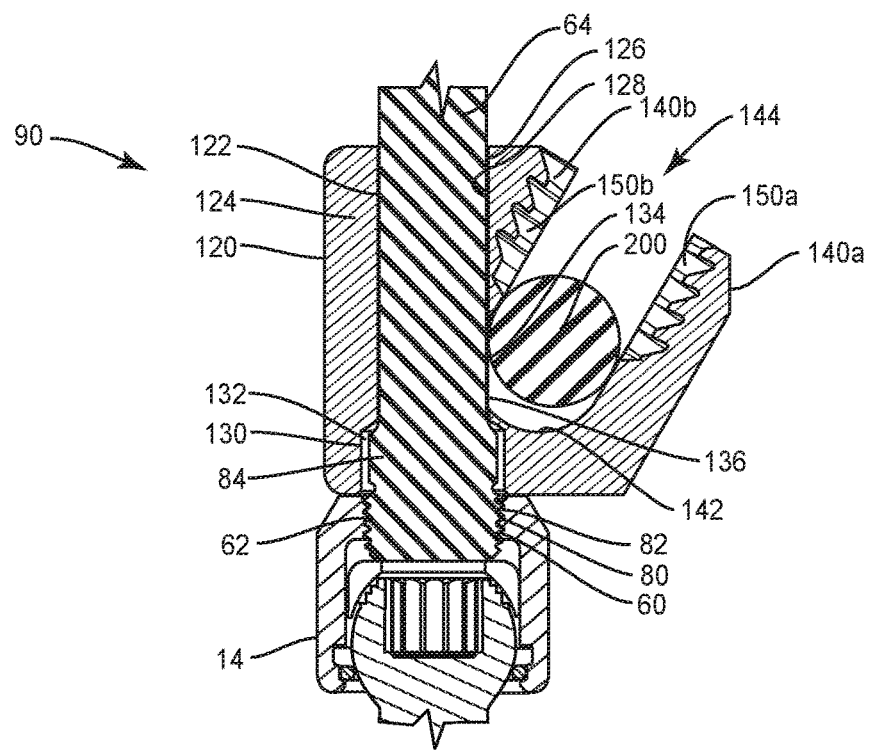
FIG. 11 is a cross section view of the components shown in FIG. 10.
Figure 12:
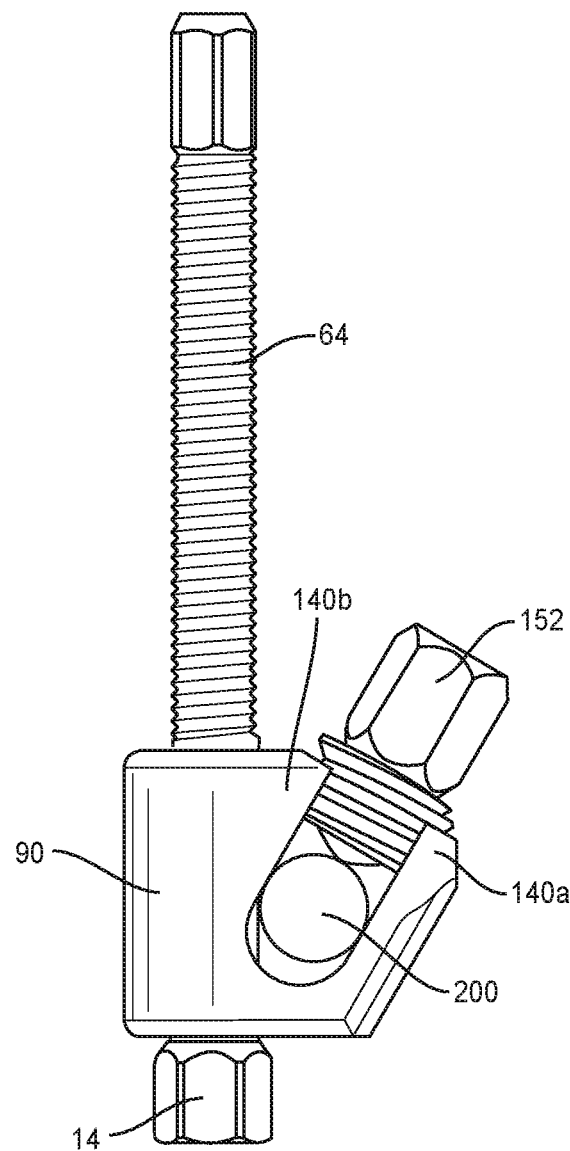
FIG. 12 is a side view of components of one embodiment of a surgical system in accordance with the principles of the present disclosure.

Post 64 includes an outer surface 80. Surface 80 includes a thread form 82, as shown in FIG. 11, configured for engagement with surface 60. In some embodiments, thread form 82 is continuous along surface 80. In some embodiments, thread form 82 may include a single thread turn or a plurality of discrete threads. In some embodiments, other penetrating elements, such as, for example, a nail configuration, barbs, expanding elements, raised elements, ribs, and/or spikes are utilized to facilitate engagement of post 64 with adaptor 14.

In some embodiments, post 64 includes a portion 84 configured for engagement with a portion of a body, such as, for example, a connector 90, as described herein. In some embodiments, portion 84 includes a hexagonal geometry configured for engagement with a similarly shaped portion of connector 90, as described herein. In some embodiments, portion 84 includes a cruciform, phillips, square, hexalobe, polygonal or star cross sectional configuration for disposal of a correspondingly shaped portion of connector 90.

In some embodiments, post 64 includes a counter torque portion 84. In some embodiments, portion 84 includes a hexagonal geometry configured for engagement with a similarly shaped portion of a body, such as, for example, a connector 90, as described herein. In some embodiments, portion 84 includes a cruciform, phillips, square, hexalobe, polygonal or star cross sectional configuration for disposal of a correspondingly shaped portion of connector 90.

In some embodiments, portion 72 includes an end 86 having a hexagonal geometry configured for engagement with a similarly shaped surgical tool, such as, for example, a portion of a driver (not shown). In some embodiments, end 86 includes a cruciform, phillips, square, hexalobe, polygonal or star cross sectional configuration for disposal of a correspondingly shaped portion of a tool. In some embodiments, end 86 includes a break off or fracture surface, as described herein, for example when torsion is applied to post 64 to fix adaptor 14 with bone screw 100, as described herein. In some embodiments, post 64 may include one or a plurality of break off or fracture surfaces. In some embodiments, post 64 may include a first break off or fracture surface having a first predetermined torque and force limit and a second break off or fracture surface having a second predetermined torque and force limit. In some embodiments, the limits may be equal, the same or different, for example, end 86 may have a lower the predetermined torque and force limit relative to portion 72.

Post 64 is actuated for fixation with adaptor 14 and bone screw 100 to fix or release bone screw 100 and adaptor 14. Post 64 is configured for engagement with crown 42 and/or head 102 to facilitate fixation of bone screw 100 with adaptor 14. Post 64 is disposable between a non-locking orientation such that bone screw 100 is moveable relative to adaptor 14 and a locked orientation such that post 64 fixes bone screw 100 with adaptor 14 relative to one or more components of spinal construct 12 and/or tissue.

In some embodiments, post 64 is pre-assembled with adaptor 14, for example, post 64 can be connected with adaptor 14 in-situ or on a back table of an operating room during a surgical procedure, or at a manufacturing facility. In some embodiments, post 64 is integrally connected with adaptor 14. In some embodiments, post 64 is connected with crown 42 such that actuation of post 64 simultaneously axially translates post 64 and crown 42 relative to adaptor 14 to fix position and/or orientation of bone screw 100 within cavity 20 relative to one or more components of spinal construct 12 and/or tissue.

Connector 90 includes a body 120 having a wall 124. Body 120 includes a surface 126 that defines a portion of a cavity 128. Cavity 128 is configured for disposal of post 64. In some embodiments, cavity 128 includes a surface 130 that defines a socket 132 configured for engagement with portion 84 in a counter torque configuration, as shown in FIG. 11. Connector 90 is configured for translation along post 64 to facilitate reduction of spinal rod 200 and orientation of tissue relative to spinal rod 200, as described herein.

Wall 124 includes a surface 134 that defines an opening 136. Opening 136 is oriented in communication with cavity 128. Opening 136 is configured to facilitate fixation of connector 90 with post 64 by engagement of a spinal implant, such as, for example, a spinal rod 200, as described herein.

Wall 124 includes extensions 140*a*, 140*b*. Extensions 140*a*, 140*b* are disposed in a spaced apart relation. Extensions 140*a*, 140*b* extend transverse to wall 124. In some embodiments, extension 140*a* and/or extension 140*b* may be disposed at alternate orientations, relative to wall 124, such as, for example, perpendicular and/or other angular orientations such as acute or obtuse, coaxial and/or may be offset or staggered. Extensions 140*a*, 140*b* and a surface 142 define a cavity, such as, for example, a passageway 144. Passageway 144 is configured for disposal of spinal rod 200. Passageway 144 is configured to facilitate loading of spinal rod 200 to connect spinal rod 200 with spinal construct 12, as described herein. In some embodiments, surface 142 includes an arcuate configuration to facilitate engagement with spinal rod 200.

In some embodiments, passageway 144 is disposed separate and apart from cavity 128. In some embodiments, passageway 144 is disposed in a side by side orientation relative to cavity 128. In some embodiments, passageway 144 is disposed in a parallel orientation relative to cavity 128. In some embodiments, passageway 144 is disposed transverse to cavity 128. In some embodiments, passageway 144 may be disposed in various orientations, such as, for example, perpendicular, transverse and/or at angular orientations, such as acute or obtuse relative to cavity 128. In some embodiments, passageway 144 may be disposed offset or staggered from cavity 128. In some embodiments, passageway 144 may have various cross section configurations, such as, for example, oval, oblong, triangular, rectangular, square, polygonal, irregular, uniform, non-uniform, variable and/or tapered. In some embodiments, surface 142 may include gripping elements or surfaces that can be, for example, rough, arcuate, undulating, mesh, porous, semi-porous, dimpled and/or textured to facilitate engagement with spinal rod 200.

Extensions 140, 140*a* include threaded surfaces 150*a*, 150*b* configured for engagement with a coupling member, such as, for example, a set screw 152. Set screw 152 is configured for engagement with spinal rod 200 to facilitate fixation and/or locking of spinal rod 200 with connector 90 and/or post 64. Set screw 152 is disposable between a non-locking orientation such that spinal rod 200 is translatable relative to spinal construct 12 and a locked orientation such that set screw 152 fixes spinal rod 200 with connector 90 and/or post 64.

Figure 13:
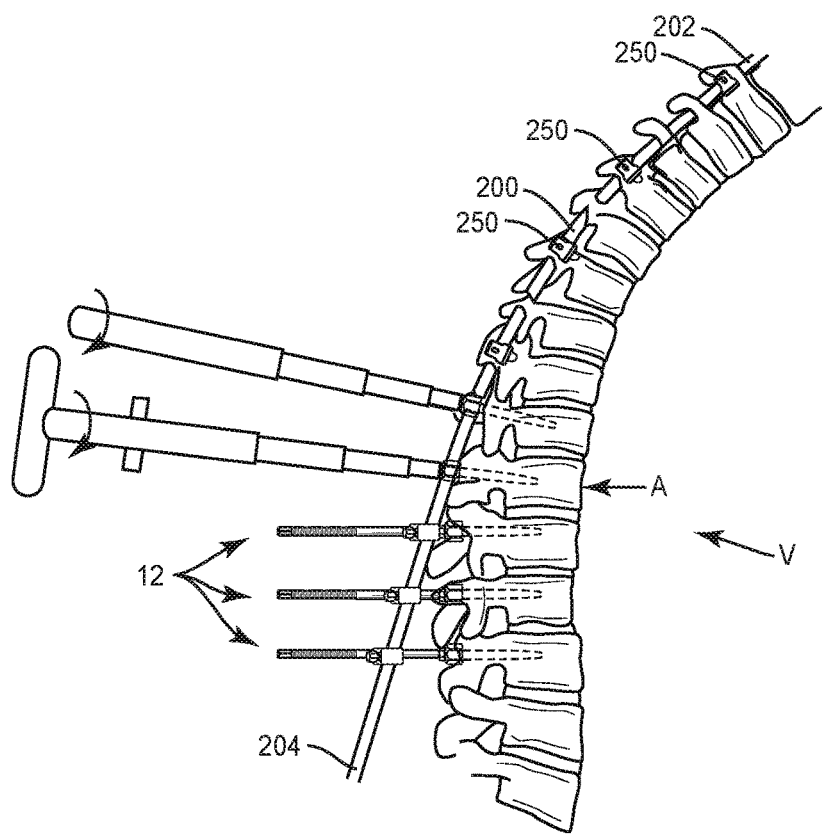
FIG. 13 is a side view of components of one embodiment of a surgical system in accordance with the principles of the present disclosure disposed with vertebrae.
Figure 14:
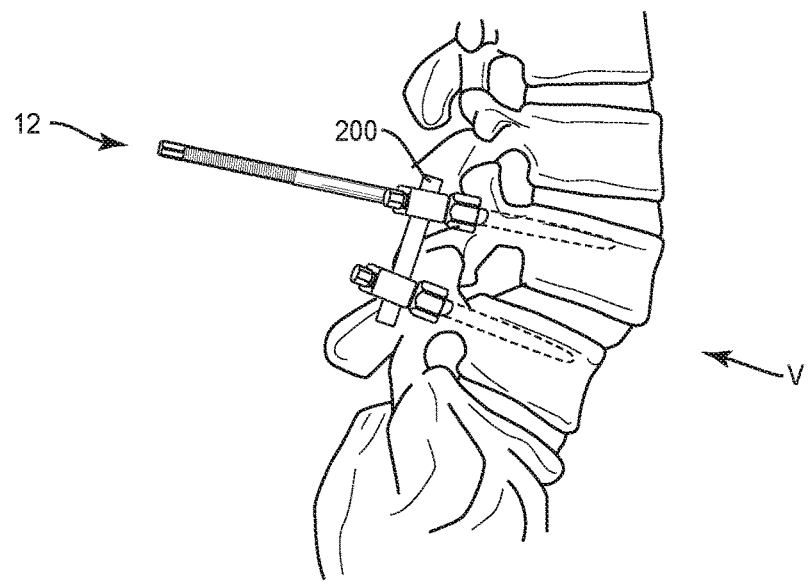
FIG. 14 is a side view of components of one embodiment of a surgical system in accordance with the principles of the present disclosure disposed with vertebrae.
Figures 15, 16:
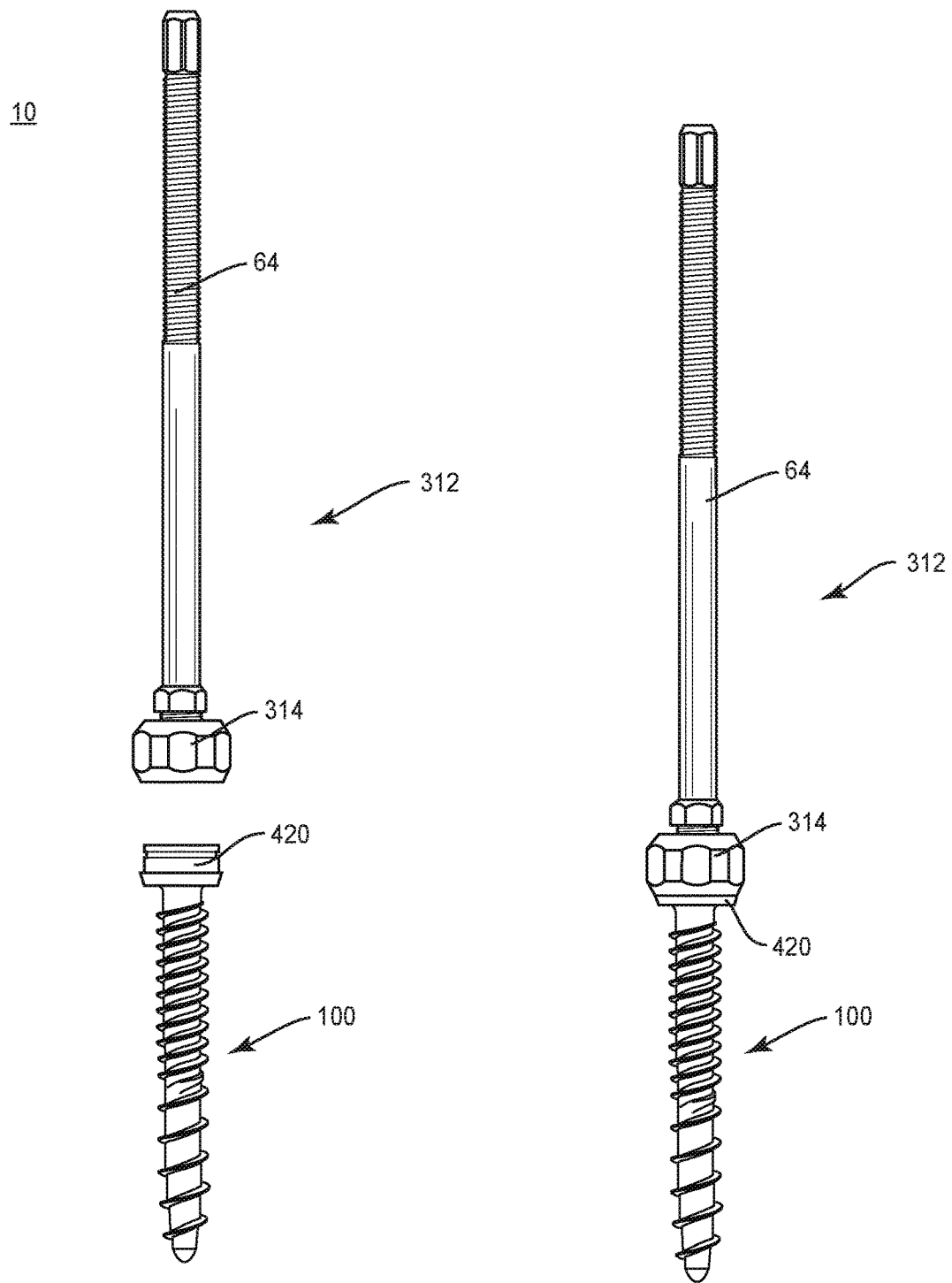
FIG. 15 is a side view of components of one embodiment of a surgical system in accordance with the principles of the present disclosure with parts separated.
FIG. 16 is a side view of the components shown in FIG. 15.

Connector 90 translates along post 64 to facilitate loading of spinal rod 200 with connector 90 and/or disposal of one or more components of spinal construct 12 with tissue. Spinal rod 200 is disposable within passageway 144 and a portion of spinal rod 200 is disposed within opening 136. Spinal rod 200 is fixed with spinal construct 12 by set screw 152. Post 64, as shown in FIGS. 13 and 14, is utilized to draw and/or pull tissue, such as, for example, vertebrae, in a direction shown by arrow A in FIG. 13 to facilitate engagement of spinal rod 200 and connector 90 and/or reduction of spinal rod 200 and/or orientation of spinal construct 12 relative to the vertebrae. Engagement of set screw 152 causes spinal rod 200 to apply a force to post 64 for an interference and/or frictional engagement therewith to compress and/or crimp post 64 between surface 206 and surface 126 to resist and/or prevent translation of connector 90 and/or spinal rod 200 relative to post 64 In some embodiments, this configuration facilitates dorsal reduction.

Figure 3:
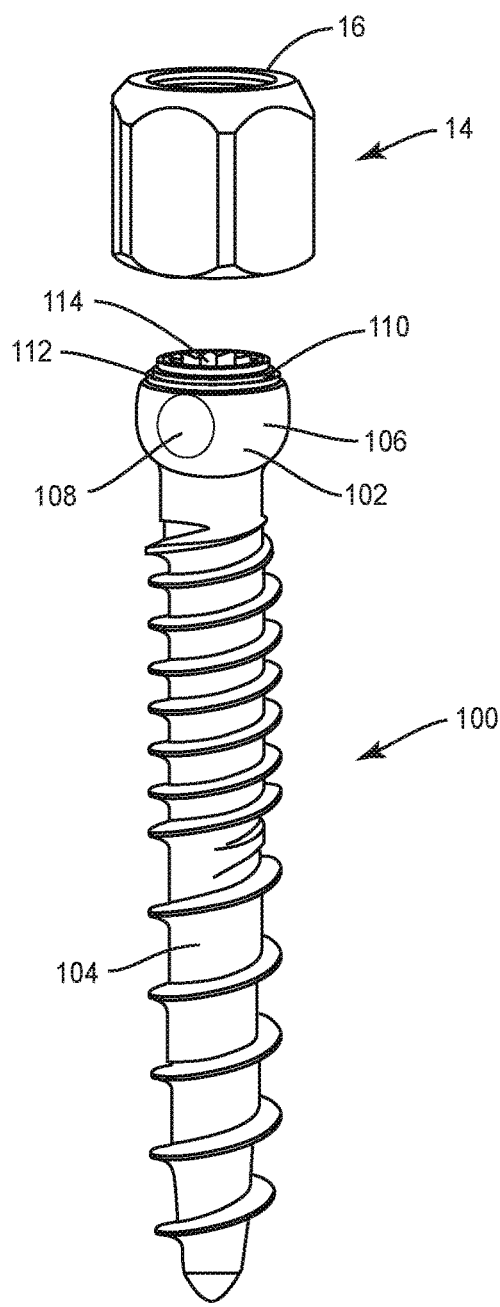
FIG. 3 is a perspective view of the components shown in FIG. 1 with parts separated.

Bone screw 100 includes head 102 having a spherical configuration such that bone screw 100 is connected with adaptor 14 in a multi-axial configuration. In some embodiments, head 102 includes a mating surface, such as, for example, arcuate surfaces 106 and planar surfaces 108, as shown in FIG. 3, configured to mate with the mating element of engagement surface 36, as described herein. In some embodiments, head 102 is slidably engageable with surface 36 in a keyed connection such that shaft 104 is rotatable along a single axis and/or within a single plane relative to adaptor 14. In some embodiments, bone screw 100 is configured for a snap fit and/or pop fit with surface 36 to facilitate engagement with adaptor 14.

In some embodiments, head 102 includes a surface 110 that defines a plurality of ridges 112 to improve purchase of head 102 with crown 42. Head 102 includes a tool engaging portion 114 configured to engage a surgical tool or instrument, as described herein. In some embodiments, portion 114 includes a hexagonal cross-section to facilitate engagement with a surgical tool or instrument, as described herein. In some embodiments, portion 114 may have alternative cross-sections, such as, for example, rectangular, polygonal, hexalobe, oval, or irregular.

Shaft 104 is configured to penetrate tissue, such as, for example, bone. In some embodiments, shaft 104 includes an outer surface having an external thread form. In some embodiments, the external thread form may include a single thread turn or a plurality of discrete threads.

In some embodiments, adaptor 14 is manually engageable with head 102 in a non-instrumented assembly such that ring 24 translates from disposal with channel 30 and into channel 32, as described herein. In some embodiments, manual engagement and/or non-instrumented assembly of adaptor 14 and head 102 includes coupling without use of separate and/or independent instrumentation engaged with the components to effect assembly. In some embodiments, manual engagement and/or non-instrumented assembly includes a practitioner, surgeon and/or medical staff grasping adaptor 14 and bone screw 100 and forcibly assembling the components. In some embodiments, manual engagement and/or non-instrumented assembly includes a practitioner, surgeon and/or medical staff grasping adaptor 14 and bone screw 100 and forcibly snap fitting the components together, as described herein. In some embodiments, manual engagement and/or non-instrumented assembly includes a practitioner, surgeon and/or medical staff grasping adaptor 14 and bone screw 100 and forcibly pop fitting the components together and/or pop fitting adaptor 14 onto bone screw 100, as described herein. In some embodiments, a force in a range of 2-50 N is required to manually engage adaptor 14 and bone screw 100 and forcibly assemble the components. For example, a force in a range of 2-50 N is required to snap fit and/or pop fit assemble adaptor 14 and bone screw 100. In some embodiments, a force in a range of 5-10 N is required to manually engage adaptor 14 and bone screw 100 and forcibly assemble the components. For example, a force in a range of 5-10 N is required to snap fit and/or pop fit assemble adaptor 14 and bone screw 100.

Spinal rod 200 extends between and end 202 and an end 204, as shown in FIG. 13. In some embodiments, spinal rod 200 may have various cross section configurations, such as, for example, circular, oval, oblong, polygonal, irregular, uniform, non-uniform, variable, offset and/or tapered. Spinal rod 200 includes a surface 206 configured for engagement with post 64, as described herein.

In some embodiments, spinal construct 12 includes one or a plurality of bone fasteners 250. Bone fastener 250 comprises a head and an elongated shaft configured for penetrating tissue. The head of bone fastener 250 includes a receiving portion configured for disposal of spinal rod 200. In some embodiments, the head of bone fastener 250 includes tulip heads and/or bone fastener 250 comprises a pedicle screw.

In some embodiments, one or more of bone fasteners 250 and/or bone screws 100 may be engaged with tissue in various orientations, such as, for example, series, parallel, offset, staggered and/or alternate vertebral levels. In some embodiments, one or more bone fasteners 250 and/or bone screws 100 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In assembly, operation and use, as shown in FIGS. 6-14, spinal implant system 10, similar to the systems and methods described herein, includes spinal construct 12 and is employed with a surgical procedure for treating disorders of the spine, such as those described herein. In some embodiments, one or all of the components of spinal implant system 10 can be delivered as a pre-assembled device or can be assembled in situ.

A surgical treatment including spinal construct 12 can be used for correction and alignment in stabilization of a treated section of vertebrae V. In an exemplary use, a medical practitioner obtains access to a surgical site including vertebrae V via a posterior surgical approach. In some embodiments, the surgical site may be accessed in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area.

Spinal construct 12 is disposed with vertebrae V in connection with the surgical procedure. In some embodiments, one or more spinal constructs 12 are disposed in a linear orientation along vertebrae V. In some embodiments, one or more spinal constructs 12 are disposed with vertebrae V in alternate orientations relative to each other, such as, for example, parallel, perpendicular, adjacent, coaxial, arcuate, offset, staggered, transverse, angular and/or relative posterior/anterior orientations and/or at alternate vertebral levels.

Pilot holes are made in vertebrae V in a selected orientation. Bone fasteners 250 are aligned with the pilot holes and fastened with the tissue of vertebrae V. Adaptor 14 is pre-assembled with head 102 of bone screw 100 in a non-instrumented assembly on a back table of an operating room during a surgical procedure, as described herein. Assembly of adaptor 14 with head 102 includes disposing crown 42 with slot 40, ring 24 with channel 30 and aligning head 102 with adaptor 14, as descried herein. Head 102 translates through and relative to ring 24, over lip 34 into channel 32, into an expanded orientation, as described herein. Head 102 engages crown 42 and ring 24 is resiliently biased to the capture orientation such that adaptor 14 is attached with bone screw 100, as described herein. Disengagement of bone screw 100 from adaptor 14 is resisted and/or prevented.

In some embodiments, adaptor 14 can be assembled with bone screw 100 in-situ. For example, bone screw 100 is fastened with vertebrae V, as described herein, and adaptor 14 is attached with head 102 in a non-instrumented assembly, as descried herein. In another example, adapter 14 is threaded with post 64 and connector 90 in a non-instrumented assembly, as described herein, on the back table of an operating room during a surgical procedure, and the adapter 14/post 64/connector 90 assembly is attached with head 102 of an implanted bone screw 100, as described herein.

Bone screw 100 including adaptor 14 is aligned with a pilot hole and fastened with the tissue of vertebrae V. Post 64 is threaded for connection with adaptor 14. Post 64 is engaged with adaptor 14 such that thread form 82 engages surface 60. Connector 90 is loaded with and translated along post 64 to a selected position to receive spinal rod 200. Spinal rod 200 is disposed adjacent passageway 144. In some embodiments, set screw 152 is engaged with connector 90 to provisionally fix spinal rod 200 with connector 90.

A reduction instrument is engaged with post 64 and/or connector 90. The reduction instrument can be slidably engaged with post 64 for reduction and/or threadably engaged with post 64 for incremental reduction. Vertebrae V is manipulated such that the reduction instrument connected with the components of spinal construct 12 draw and/or pull bone screw 100 and vertebrae V, in a direction shown by arrow A in FIG. 13, to reduce spinal rod 200 with vertebrae V. In some embodiments, spinal rod 200 can be selectively reduced with the components of spinal construct 12 and vertebrae V such that reduction can be stopped at any point to facilitate correction and is not dependent on seating of spinal rod 200 with connector 90. In some embodiments, spinal rod 200 can be selectively reduced with the components of spinal construct 12 and vertebrae V in a selected dorsal orientation relative to vertebrae V. Spinal rod 200 is selectively reduced and/or adjusted, for example, medial/lateral adjustment and locked with set screw 152 along post 64.

Post 64 is engaged with crown 42 to fix adaptor 14 with bone screw 100 to resist and/or prevent movement of bone screw 100 relative to adaptor 14. Set screw 152 engages spinal rod 200 causing surface 206 to apply a force to post 64 to fix connector 90 with post 64. The force applied by spinal rod 200 causes an interference and/or frictional engagement with a surface of post 64 to compress and/or crimp post 64 to resist and/or prevent translation of connector 90 relative to post 64. Set screw 152 fixes the selected orientation of spinal rod 200 relative to vertebrae V. In some embodiments, post 64 is manipulated such that portion 72 is fractured, broken away and/or sheared at a selected position along post 64, as described herein.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In one embodiment, as shown in FIGS. 15-22, spinal implant system 10, similar to the systems and methods described herein, includes a spinal construct 312, similar to spinal construct 12 described herein. Spinal construct 312 includes an adaptor 314, similar to adaptor 14 described herein. Adaptor 314 includes a wall 316 having a surface 318 that defines a cavity 320. Wall 316 extends along an axis X2. Cavity 320 is configured for disposal of head 102 of bone screw 100 described herein.

Surface 318 defines a groove 322 configured for disposal of a circumferential ring 324. Ring 324 includes a circumference that extends between ends defining a gap, which facilitates expansion and contraction thereof. Groove 322 includes a circumferential channel 330 that accommodates expansion of ring 324. In some embodiments, upon disposal of ring 324 with groove 322, the surface of groove 322 resists and/or prevents axial translation of ring 324 relative to axis X2.

Ring 324 is expandable and resilient between a contracted and/or capture orientation, and an expanded orientation, similar to that described herein. Ring 324 facilitates manual engagement of adaptor 314 and bone screw 100 such that adaptor 314 is attached with bone screw 100 in a non-instrumented assembly, as described herein. In some embodiments, ring 324 is expandable and resilient between a contracted and/or capture orientation and an expanded orientation for assembly of adaptor 314 with bone screw 100, as shown and described for example with regard to FIGS. 18-22.

Surface 318 defines a slot 340 configured for disposal of a part, such as, for example, a crown 342 and a sleeve 344. Crown 342 is configured for disposal within cavity 320. Crown 342 includes a wall 346 having an end surface 348 and an end surface 350. Surface 348 is configured for engagement with post 64 described herein. Surface 350 defines a curved portion of crown 342 configured for engagement with head 102.

Surface 348 defines a flange 352 configured for mating engagement with a portion of surface 318. In some embodiments, flange 352 engages a portion of surface 318 in a keyed connection. In some embodiments, engagement of flange 352 and surface 318 prevents rotation and/or axial translation of crown 342 relative to surface 318.

Sleeve 344 includes a surface 354 that defines a cavity, such as, for example, a groove 356. In some embodiments, groove 356 extends about all or a portion of surface 354. Groove 356 includes a surface 358 and a surface 360. Surface 358 is disposed at an angle relative to axis X2 to define a ramp. Surface 360 is disposed at an angle relative to axis X2 to define a ramp. The ramps of surfaces 358, 360 are oriented in spaced apart relation. An intermediate surface 362 is disposed between the ramps. Surface 362 is substantially even and circumferentially disposed about sleeve 344. In some embodiments, the ramps of surfaces 358, 360 are selectively inclined to resist and/or prevent displacement of ring 324 from channel 330 to provisionally fix sleeve 344 with adaptor 314. In some embodiments, the inclination of the ramps of surfaces 358, 360 facilitate disengagement of ring 324 from groove 356 upon axial translation of sleeve 344, as described herein. In some embodiments, surfaces 358, 360 are oriented substantially perpendicular to axis X2. In some embodiments, groove 356 does not include inclined surfaces, as described above, and alternatively includes a protrusion or a lip configured to engage ring 324.

Figure 17:
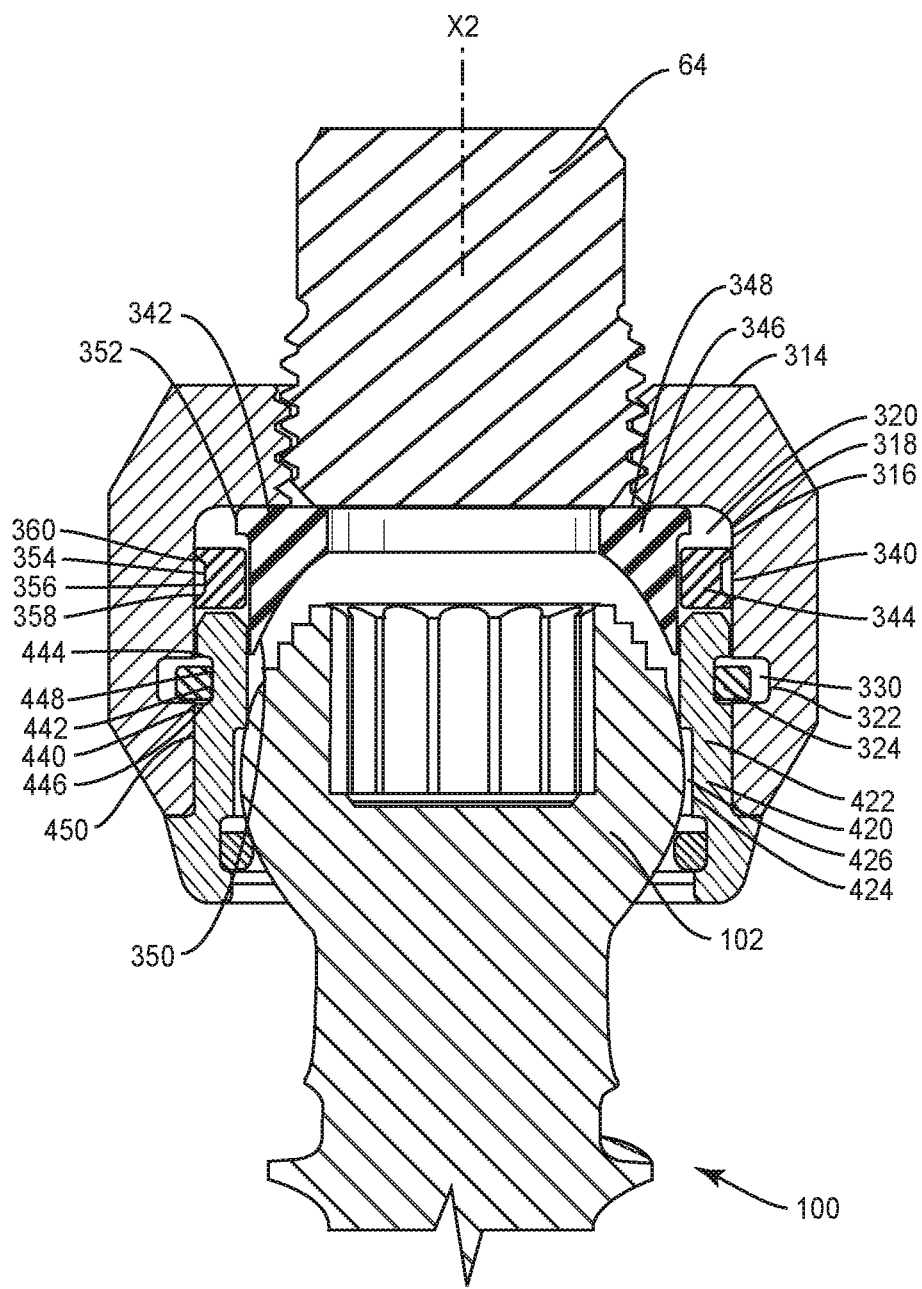
FIG. 17 is a cross section view of the components shown in FIG. 16.
Figure 18:
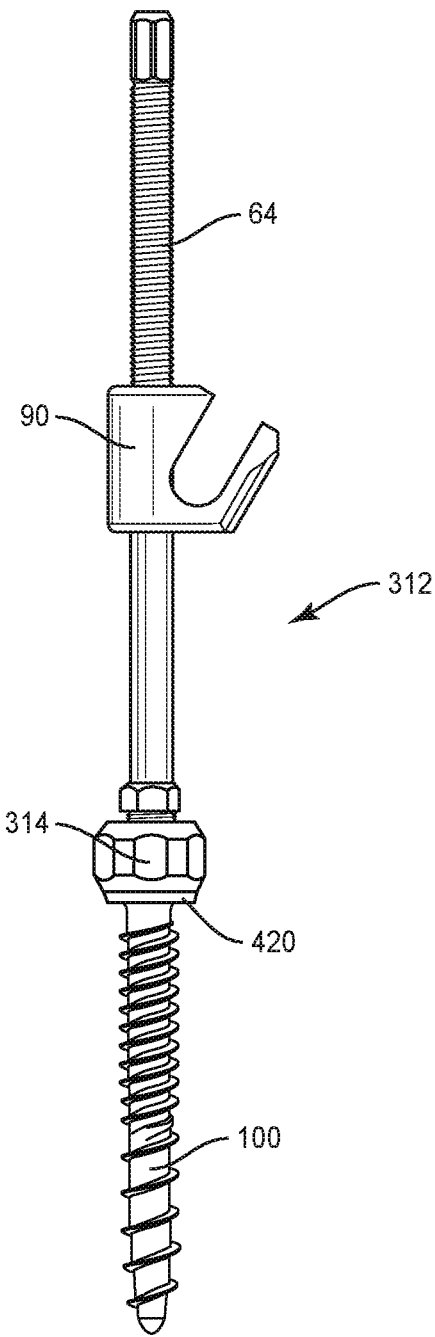
FIG. 18 is a side view of components of one embodiment of a surgical system in accordance with the principles of the present disclosure.
Figure 19:
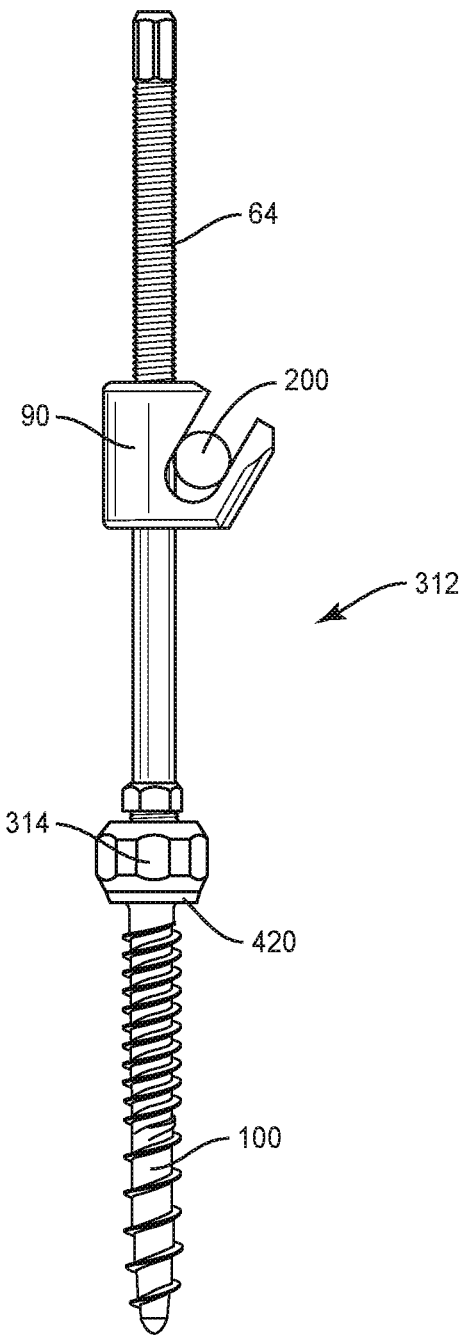
FIG. 19 is a side view of the components shown in FIG. 18.
Figure 20:
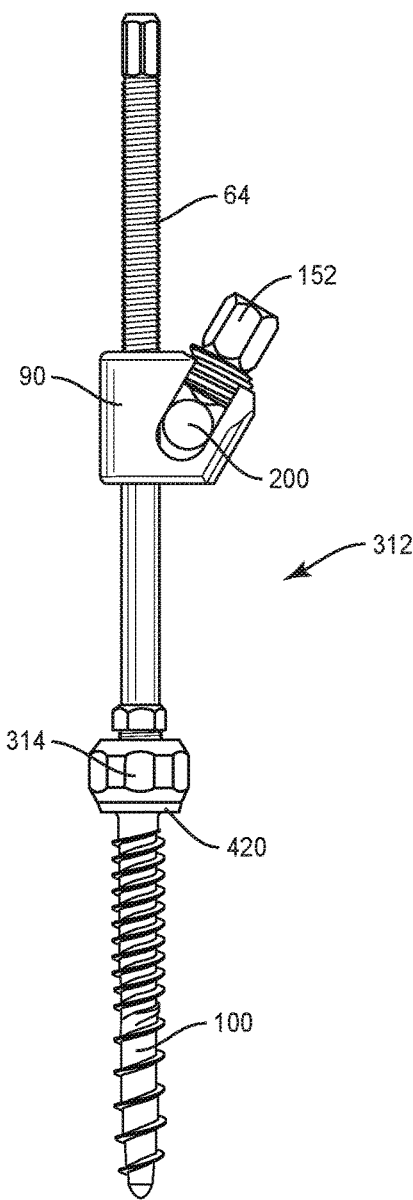
FIG. 20 is a side view of components of one embodiment of a surgical system in accordance with the principles of the present disclosure.
Figure 21:
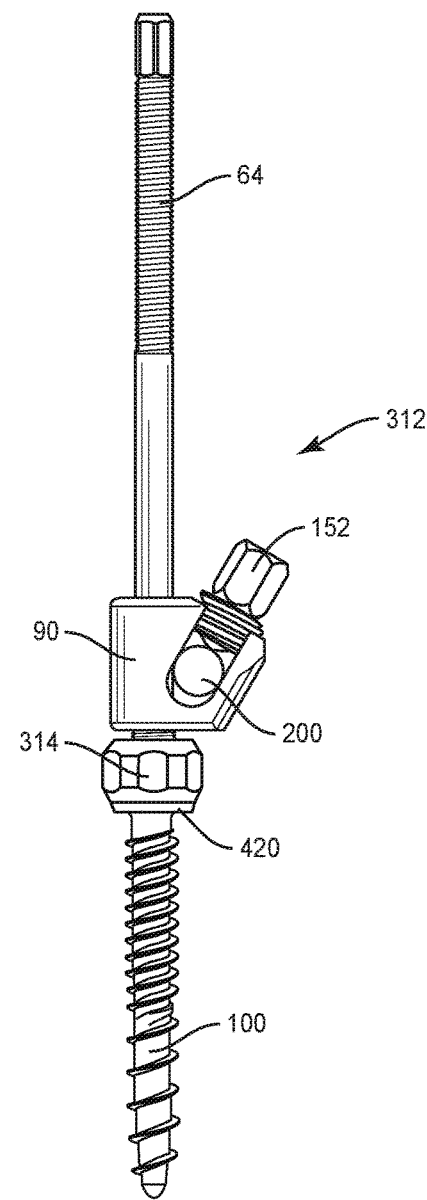
FIG. 21 is a side view of the components shown in FIG. 20.
Figure 22:
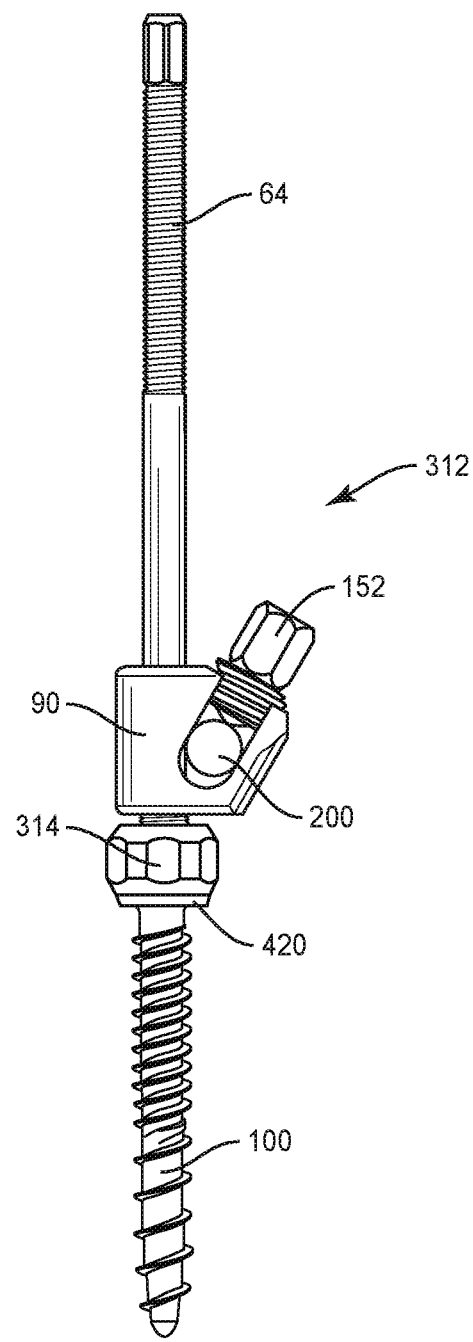
FIG. 22 is a side view of the components shown in FIG. 20.

Sleeve 344 is configured for translation within slot 340 along surface 318. Sleeve 344 translates relative to crown 342 and adaptor 314 within slot 340. Translation of sleeve 344 within slot 340 moves sleeve 344 between a configuration such that ring 324 is disposed within channel 330 and groove 356 to provisionally fix sleeve 344 relative to adaptor 314 and a configuration, as shown in FIG. 17, such that ring 324 remains disposed within channel 330 and a base 420, attached with bone screw 100, to fix bone screw 100 with adaptor 314, as described herein.

Base 420 is configured for assembly with a bone screw 100, as described herein. Base 420 includes a wall 422 having a surface 424. Surface 424 defines a cavity 426 configured for disposal of head 102. Surface 424 facilitates engagement of head 102 with base 420 via a pressure and/or force fit connection.

In some embodiments, surface 424 includes mating elements, such as, for example, index elements (not shown). In some embodiments, the index elements include a protrusion (not shown) configured to limit rotation about a single axis disposed in a plane relative to adaptor 314.

In some embodiments, adaptor 314 is connected to a selected crown 342 to comprise a multi-axial receiver. In some embodiments, adaptor 314 is connected to a selected crown 342 to comprise a uni-axial receiver. In some embodiments, adaptor 314 is connected to a selected crown 342 to comprise a fixed axis receiver to resist and/or prevent movement of shaft 104 relative to adaptor 314. In some embodiments, adaptor 314 comprises one or more fixed axis receivers, multi-axial receivers and uni-axial receivers. In some embodiments, spinal implant system 10 comprises a spinal implant kit, which includes alternate crowns, such as those described herein. In some embodiments, spinal implant system 10 comprises a spinal implant kit, which includes alternate receivers, screws and crowns.

In some embodiments, base 420 may be disposed with head 102 in alternate fixation configurations, such as, for example, friction fit, pressure fit, locking protrusion/recess, locking keyway and/or adhesive. Base 420 is configured for rotation relative to head 102. In some embodiments, base 420 is configured for rotation in range of 360 degrees relative to head 102 to facilitate positioning of shaft 104 with tissue. In some embodiments, base 420 is configured for selective rotation in range of 360 degrees relative to and about head 102 such that shaft 104 is selectively aligned for rotation in a plane relative to adaptor 314, and rotation in a second plane is resisted and/or prevented.

Wall 422 includes a surface 440. Surface 440 defines a groove 442. Groove 442 includes a surface 444 and a surface 446. Surfaces 444, 446 are oriented substantially perpendicular to axis X2. In some embodiments, surfaces 444, 446 may be disposed in various orientations and/or inclinations, such as, for example, transverse and/or at angular orientations, such as acute or obtuse relative to axis X2. Surface 444 is oriented in spaced apart relation relative to surface 446. An intermediate surface 448 is disposed between surfaces 444, 446. Surface 448 is substantially even and circumferentially disposed about groove 442. In some embodiments, surfaces 444, 446, 448 may be disposed about all or only a portion of groove 442. Groove 442 is configured for disposal of ring 324 to prevent displacement of ring 324 from channel 330 and to permanently fix adaptor 314 with bone screw 100, as shown in FIG. 17. Base 420 is configured for axial translation relative to head 102 within slot 340, as described herein.

For example, base 420 is assembled with head 102 and a surface 450 engages sleeve 344 to release sleeve 344 from ring 324. As base 420 engages sleeve 344 and translates, the ramp of surface 360 engages ring 324 and surface 360 slides over ring 324 to release sleeve 344 from ring 324. Ring 324 expands into channel 330. With ring 324 expanded into channel 330, base 420 and head 102 axially translate relative to adaptor 314 within slot 340 to align groove 442 with channel 330. Expansion of ring 324 via engagement with surface 360 facilitates axial translation of bone screw 100 into slot 340. Alignment of groove 442 with channel 330 allows ring 324 to resiliently contract to the capture orientation for disposal of ring 324 within groove 442 and channel 330. Ring 324 is fixed within channel 330 and groove 442. Surfaces 444, 446 resist and/or prevent disengagement of ring 324 from channel 330 and groove 442 to permanently assemble bone screw 100 with adaptor 314.

In assembly, operation and use, as shown in FIGS. 18-22, spinal implant system 10, similar to the systems and methods described herein, includes spinal construct 312 and is employed with a surgical procedure for treating disorders of the spine, such as those described herein.

Pilot holes are made in vertebrae V in a selected orientation. Bone fasteners 250 are aligned with the pilot holes and fastened with the tissue of vertebrae V. Adaptor 314 is threaded with post 64. Base 420 is attached with bone screw 100. The assembly of adaptor 314/post 64 is attached with base 420/head 102 in a non-instrumented assembly, as descried herein. Bone screws 100 are aligned with the pilot holes and fastened with the tissue of vertebrae V. Connector 90 is loaded with and translated along post 64 to a selected position to receive spinal rod 200. Spinal rod 200 is disposed adjacent passageway 144. In some embodiments, set screw 152 is engaged with connector 90 to provisionally fix spinal rod 200 with connector 90.

A reduction instrument is engaged with post 64 and/or connector 90, as described herein. Vertebrae V is manipulated such that the reduction instrument connected with the components of spinal construct 312 draw and/or pull bone screw 100 and vertebrae V to reduce spinal rod 200 with vertebrae V. In some embodiments, spinal rod 200 can be selectively reduced with the components of spinal construct 312 and vertebrae V, similar to that described herein. Spinal rod 200 is selectively reduced and/or adjusted and locked with set screw 152 along post 64.

Post 64 is engaged with crown 342 to fix adaptor 314 with bone screw 100 to resist and/or prevent movement of bone screw 100 relative to adaptor 314. Set screw 152 engages spinal rod 200 causing surface 206 to apply a force to post 64 to fix connector 90 with post 64. The force applied by spinal rod 200 causes an interference and/or frictional engagement with a surface of post 64 to compress and/or crimp post 64 to resist and/or prevent translation of connector 90 relative to post 64. Set screw 152 fixes the selected orientation of spinal rod 200 relative to vertebrae V.

Figure 23:
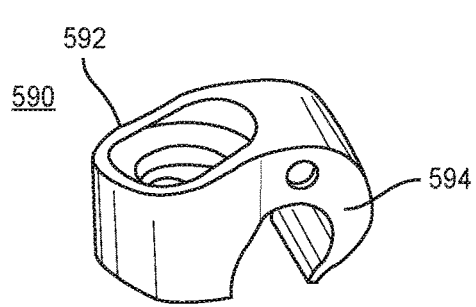
FIG. 23 is a perspective view of components of one embodiment of a surgical system in accordance with the principles of the present disclosure.
Figure 24:
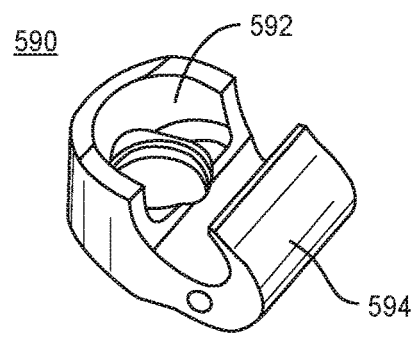
FIG. 24 is a perspective view of the components shown in FIG. 23.

In one embodiment, as shown in FIGS. 23 and 24, spinal implant system 10, similar to the systems and methods described herein, includes a connector 590, similar to connector 90 described herein. Connector 590 includes a body 592 that slidably translates along post 64 and an arcuate extension 594 for disposal of spinal rod 200.

Figure 25:
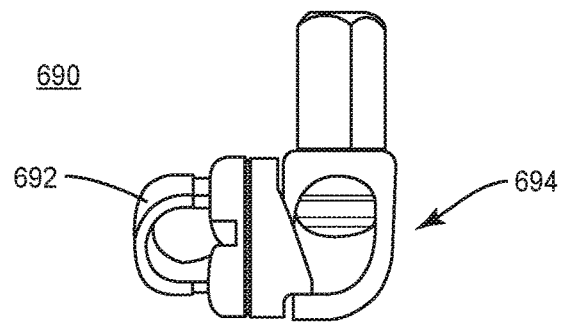
FIG. 25 is a side view of components of one embodiment of a surgical system in accordance with the principles of the present disclosure.

In one embodiment, as shown in FIG. 25, spinal implant system 10, similar to the systems and methods described herein, includes a connector 690, similar to connector 90 described herein. Connector 690 includes a body 692 that slidably translates along post 64 and a circular extension 694 for disposal of spinal rod 200. Body 692 is coupled with extension 694 via a splined connection for selective rotatable orientation of extension 694.

Figure 26:
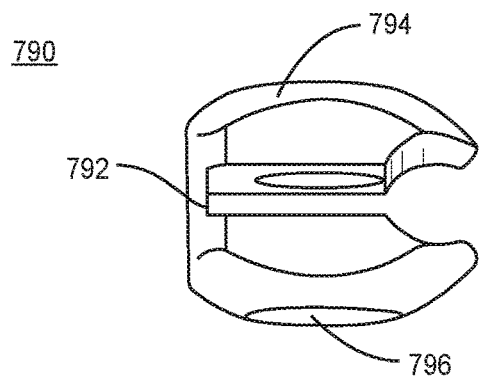
FIG. 26 is a side view of components of one embodiment of a surgical system in accordance with the principles of the present disclosure.

In one embodiment, as shown in FIG. 26, spinal implant system 10, similar to the systems and methods described herein, includes a connector 790, similar to connector 90 described herein. Connector 790 includes a body 792 that slidably translates along post 64 and extensions 794, 796 for disposal of spinal rod 200. Extensions 794, 796 are relatively movable for capture of spinal rod 200.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
 a fastener having a head and a shaft;
 a member including an inner surface defining a groove and a cavity configured for disposal of the head;
 a band positioned within the groove and engageable with the head to maintain the head in the cavity;
 a longitudinal element connectable to the member, the longitudinal element including opposite first and second ends and an intermediate portion between the first end and the second end, the first end including a first portion having a hexagonal geometry, the second end including a second portion having a diameter greater than a diameter of the first portion, the intermediate portion including a threaded section and a non-threaded section between the threaded section and the second portion;
 a body defining a passageway, the body including a first extension disposed in spaced apart relation from a second extension, the extensions defining an implant cavity in communication with the passageway, the longitudinal element extending through the passageway; and
 a coupling member engageable with the body,
 wherein the shaft is movable relative to the head between a first orientation in which the shaft is coaxial with the longitudinal element and a second orientation in which the shaft extends transverse to the longitudinal element.

2. A spinal construct as recited in claim 1, wherein the passageway includes a counter torque socket engageable with a counter torque portion of the longitudinal element in a counter torque configuration.

3. A spinal construct as recited in claim 1, further comprising a spinal rod disposed with the implant cavity such that the coupling member engages the spinal rod and the spinal rod engages the longitudinal element to fix the body with the longitudinal element.

4. A spinal construct as recited in claim 1, wherein the longitudinal element includes a frangible portion.

5. A spinal construct as recited in claim 1, further comprising a part disposable between the longitudinal element and the head, the part being disposed about the head and defining an opening that communicates with a socket of the head.

6. A spinal construct as recited in claim 1, wherein the longitudinal element is engageable with a crown disposed with the member to fix an orientation of the fastener relative to the member.

7. A spinal construct as recited in claim 1, wherein the band is expandable between a capture orientation and an expanded orientation.

8. A spinal construct as recited in claim 1, wherein the member is manually engageable with the fastener to connect the member and the fastener.

9. A spinal construct as recited in claim 1, wherein the member is engageable with the head in a snap-fit assembly.

10. A spinal construct as recited in claim 1, wherein the member is engageable with the head in a pop-on assembly.

11. A spinal construct as recited in claim 1, wherein the head is engageable with the member such that the shaft is configured for a selected movement that includes the fastener being moveable about a plurality of axes relative to the member.

12. A spinal construct as recited in claim 1, wherein the head is engageable with the member such that the shaft is configured for a selected movement that includes the fastener being moveable about a single axis relative to the member.

13. A spinal construct as recited in claim 1, wherein the body includes opposite planar top and bottom end surfaces, the implant cavity extending through the top end surface without extending through the bottom end surface.

14. A spinal construct as recited in claim 1, further comprising a spinal rod disposed in the implant cavity, the spinal rod being spaced apart from the member by the body and the longitudinal element, the implant cavity being U-shaped.

15. A spinal construct as recited in claim 1, wherein the second portion includes a threaded outer surface configured for engagement with a threaded inner surface of the member to couple the longitudinal element to the member.

16. A spinal construct comprising:
a fastener including a head and a shaft;
an adaptor including an inner surface defining a groove and a cavity for disposal of the head, the adaptor comprising a threaded inner surface defining a first opening and an unthreaded inner surface defining a second opening, the openings being in communication with the cavity, the head having a maximum diameter greater than a maximum diameter of the first opening and less than a maximum diameter of the second opening to allow the head to be bottom loaded into the cavity;
an expandable ring being disposable with the groove and engageable with the head to connect the fastener and the adaptor;
a post threadably attachable with the adaptor, the post comprising a threaded outer surface engaged with the threaded inner surface, the post including opposite first and second ends and an intermediate portion between the first end and the second end, the first end including a first portion having a hexagonal geometry, the second end including a second portion having the threaded outer surface, the second portion having a diameter greater than a diameter of the first portion, the intermediate portion including a threaded section and a non-threaded section between the threaded section and the second portion;
a crown disposable between the post and the head;
a connector that defines a passageway for disposal of the post and being translatable relative thereto, the connector including a first extension disposed in spaced apart relation from a second extension, the extensions defining a U-shaped implant cavity in communication with the passageway;
a set screw including a threaded outer surface engageable with threaded inner surfaces of the extensions; and
a spinal rod disposed with the implant cavity such that the spinal rod engages the post and the set screw engages the spinal rod to fix the connector with the post, the spinal rod being spaced apart from the adaptor by the connector and the post.

17. A spinal construct as recited in claim 16, wherein the passageway includes a counter torque socket engageable with a counter torque portion of the post in a counter torque configuration.

18. A spinal construct as recited in claim 16, wherein the groove includes a first circumferential channel having a first diameter and a second circumferential channel having a second diameter that is greater than the first diameter, the second circumferential channel being separated from the first circumferential channel by a lip.

19. A spinal construct as recited in claim 16, wherein the crown includes a socket that is coaxial with a socket of the head, the post being coaxial with the sockets.

20. A spinal implant system comprising:
a plurality of alternate adaptors each including a cavity and a groove comprising a first channel and a second channel separated from the first channel by a protrusion;
a fastener including a head engageable with a receiver such that the fastener is compatible with the plurality of adaptors, wherein an adaptor is selected for connection with the head to comprise a spinal construct having a selected movement;
a ring disposed in one of the first channels and configured to translate over a respective one of the protrusions and into a respective one of the second channels to maintain the head in a respective one of the cavities;
a longitudinal element connectable to the adaptor, the longitudinal element including opposite first and second ends and an intermediate portion between the first end and the second end, the first end including a first portion having a hexagonal geometry, the second end including a second portion having a diameter greater than a diameter of the first portion, the intermediate portion including a threaded section and a non-threaded section between the threaded section and the second portion;
a body defining a passageway for disposal the longitudinal element, the body including a first extension disposed in spaced apart relation from a second extension, the extensions defining a U-shaped implant cavity in communication with the passageway;
a coupling member including a threaded outer surface engageable with threaded inner surfaces of the extensions; and
a spinal rod disposed with the implant cavity such that the spinal rod engages the longitudinal element and the coupling member engages the spinal rod to fix the body with the longitudinal element, the spinal rod being spaced apart from the adaptor by the body and the longitudinal element.

* * * * *